US010321663B2

(12) United States Patent
Horton et al.

(10) Patent No.: US 10,321,663 B2
(45) Date of Patent: Jun. 18, 2019

(54) AGRICULTURAL DRONE FOR USE IN LIVESTOCK MONITORING

(71) Applicant: Digi-Star, LLC, Oakland, NJ (US)

(72) Inventors: Christopher V. Horton, Stoughton, WI (US); Samuel R. Vorpahl, Fort Atkinson, WI (US)

(73) Assignee: DIGI-STAR, LLC, Fort Atkinson, WI (US)

( * ) Notice: Subject to any disclaimer, the term of this patent is extended or adjusted under 35 U.S.C. 154(b) by 347 days.

(21) Appl. No.: 14/864,222

(22) Filed: Sep. 24, 2015

(65) Prior Publication Data

US 2017/0086428 A1    Mar. 30, 2017

(51) Int. Cl.
| H04N 7/18 | (2006.01) |
| A01K 29/00 | (2006.01) |
| B64C 39/02 | (2006.01) |
| G06K 9/00 | (2006.01) |
| A61B 5/00 | (2006.01) |
| A61B 5/01 | (2006.01) |
| B64D 47/08 | (2006.01) |

(52) U.S. Cl.
CPC .......... *A01K 29/005* (2013.01); *A61B 5/0008* (2013.01); *A61B 5/0015* (2013.01); *A61B 5/01* (2013.01); *B64C 39/024* (2013.01); *G06K 9/0063* (2013.01); *G06K 9/00771* (2013.01); *H04N 7/185* (2013.01); *A61B 5/0075* (2013.01); *A61B 5/0077* (2013.01); *A61B 5/6887* (2013.01); *A61B 5/6896* (2013.01); *A61B 2503/40* (2013.01); *B64C 2201/127* (2013.01); *B64D 47/08* (2013.01)

(58) Field of Classification Search
CPC ............ A01K 29/005; B64C 2201/127; B64C 39/024; B64D 47/08
See application file for complete search history.

(56) References Cited

U.S. PATENT DOCUMENTS

| 3,781,837 A | 12/1973 | Anderson |
| 3,893,111 A | 7/1975 | Cotter |
| 4,148,278 A | 4/1979 | Anderson |
| 4,399,821 A | 8/1983 | Bowers |
| 4,844,076 A | 7/1989 | Lesho et al. |
| 4,854,328 A | 8/1989 | Pollack |
| 4,865,044 A | 9/1989 | Wallace et al. |

(Continued)

FOREIGN PATENT DOCUMENTS

| CN | 103299975 A | 9/2013 |
| CN | 103723275 A | 4/2014 |

(Continued)

OTHER PUBLICATIONS

Anonymous: "PrecisionHawkTurn Applications into Data: Livestock Management PrecisionHawk", precisionhawk.com, Jul. 15, 2014 (Jul. 15, 2014), XP055314971.*

(Continued)

*Primary Examiner* — Md N Haque
(74) *Attorney, Agent, or Firm* — Chiesa Shahinian & Giantomasi PC

(57) ABSTRACT

A method and system utilizing one or more agricultural drones to improve the real-time monitoring, measuring and analysis of the health of livestock, in particular, the core body temperatures thereof.

32 Claims, 7 Drawing Sheets

(56) References Cited

U.S. PATENT DOCUMENTS

| | | | |
|---|---|---|---|
| 5,008,821 A | | 4/1991 | Pratt et al. |
| 5,424,957 A | | 6/1995 | Kerkhoff et al. |
| 5,474,085 A | | 12/1995 | Hurnik et al. |
| 5,751,576 A | | 5/1998 | Monson |
| 5,974,348 A | | 10/1999 | Rocks |
| 5,984,875 A | | 11/1999 | Brune |
| 6,032,084 A | * | 2/2000 | Anderson ............ A01K 29/00 348/E13.004 |
| 6,059,733 A | | 5/2000 | Brune et al. |
| 6,099,482 A | | 8/2000 | Brune et al. |
| 6,445,983 B1 | | 9/2002 | Dickson et al. |
| 6,529,615 B2 | | 3/2003 | Hendrickson et al. |
| 7,479,884 B1 | | 1/2009 | Fullerton |
| 7,536,976 B1 | | 5/2009 | Bryant |
| 7,689,434 B2 | | 3/2010 | Cureton et al. |
| 8,297,231 B2 | | 10/2012 | Yanai et al. |
| 8,442,765 B1 | | 5/2013 | Ingvalson |
| 8,588,887 B2 | | 11/2013 | Arneson et al. |
| 8,730,014 B2 | | 5/2014 | Fullerton |
| 9,037,521 B1 | | 5/2015 | Mewes et al. |
| 2002/0010390 A1 | | 1/2002 | Guice et al. |
| 2004/0162638 A1 | | 8/2004 | Solomon |
| 2007/0208442 A1 | | 9/2007 | Perrone |
| 2008/0059263 A1 | * | 3/2008 | Stroman ............ G06Q 10/063 705/7.25 |
| 2009/0187392 A1 | * | 7/2009 | Riskey ................ A01K 11/007 703/11 |
| 2009/0294573 A1 | | 12/2009 | Wilson et al. |
| 2009/0299496 A1 | | 12/2009 | Cade |
| 2010/0017046 A1 | | 1/2010 | Cheung et al. |
| 2012/0022719 A1 | | 1/2012 | Matos |
| 2012/0101861 A1 | | 4/2012 | Lindores |
| 2012/0109614 A1 | | 5/2012 | Lindores |
| 2012/0310532 A1 | | 12/2012 | Snoeck et al. |
| 2013/0173321 A1 | * | 7/2013 | Johnson ................ G06Q 10/06 705/7.12 |
| 2013/0231968 A1 | | 9/2013 | Wiliness |
| 2014/0024313 A1 | | 1/2014 | Campbell |
| 2014/0035752 A1 | | 2/2014 | Johnson |
| 2014/0089045 A1 | | 3/2014 | Johnson |
| 2014/0095261 A1 | | 4/2014 | Johnson |
| 2014/0155756 A1 | | 6/2014 | Elazari-Volcani |
| 2014/0188573 A1 | | 7/2014 | Avey et al. |
| 2014/0222246 A1 | | 8/2014 | Mohamadi |
| 2014/0303814 A1 | | 10/2014 | Burema et al. |
| 2014/0316614 A1 | | 10/2014 | Newman |
| 2015/0037307 A1 | | 2/2015 | Bralkowski et al. |
| 2015/0106434 A1 | | 4/2015 | Fiene et al. |
| 2016/0050840 A1 | | 2/2016 | Sauder et al. |
| 2016/0093212 A1 | * | 3/2016 | Barfield, Jr. ........... H04N 7/185 348/144 |

FOREIGN PATENT DOCUMENTS

| | | |
|---|---|---|
| CN | 103770943 A | 5/2014 |
| CN | 203652111 U | 6/2014 |
| DE | 102010046479 A1 | 3/2012 |
| DE | 102014201203 A1 | 7/2015 |
| WO | 2008097080 | 8/2008 |
| WO | 2008098290 A1 | 8/2008 |
| WO | 2010057266 | 5/2010 |
| WO | 2013041636 A1 | 3/2013 |
| WO | 2014058337 A1 | 4/2014 |
| WO | 2014146884 A1 | 9/2014 |
| WO | 2015142166 A1 | 9/2015 |
| WO | 2016123201 A1 | 8/2016 |

OTHER PUBLICATIONS

Anonymous: "PrecisionHawkTurn Applications into Data: Livestock Management PrecisionHawk", precisionhawk.com, Jul. 15, 2014 (Jul. 15, 2014), XP055314971 (Year: 2014).*

International Search Report and Written Opinion dated Sep. 27, 2016 in connection with International Patent Application No. PCT/US2016/041705, 9 pages.

International Search Report and Written Opinion dated Nov. 9, 2016 in connection with International Application No. PCT/US2016/051673, 19 pages.

Krissa Welshans, "Sky's the Limit for UAVs in Ag—Feedstuffs Foodlink," published on Mar. 27, 2015; URL: http://feedstuffsfoodlink.com.story-skys-limit-uavs-ag-0-125732-printversion; retrieved on Dec. 5, 2016.

"PrecisionHawk>Turn Applications into Data: Livestock Management PrecisionHawk,"; precisionhawk.com, Jul. 15, 2014, XP0555314971, URL: http://media.precisionhawk.com/topic/turn-applications-into-data-livestock-management; retrieved on Oct. 28, 2016.

International Search Report and Written Opinion dated Nov. 25, 2016 in connection with International Application No. PCT/US2016/051584, 14 pages.

"Unmanned Aerial Vehicles, Farming and Cattle", Penn State Extension, published on Feb. 24, 2015; URL:http://extension.psu.edu/animals/dairy/news/2015/unmanned-aerial-vehicles-farming-and-cattle; retrieved on Dec. 5, 2016.

Lee Jesperson, "Flying Drone Around the Feedlot," Published on Dec. 27, 2014; URL://www.youtube.com/watch?v=K122WAURDY; retrieved on Oct. 31, 2016.

Utility U.S. Appl. No. 14/860,072, filed Sep. 21, 2015.

Utility U.S. Appl. No. 14/859,974, filed Sep. 21, 2015.

International Search Report and Written Opinion dated Feb. 9, 2017 in connection with International Application No. PCT/US2016/059626, 12 pages.

"Drones for Agricultural Crop Surveillance," Precision Drone, Agriculture, retrieved on May 20, 2015, from http://www.precisiondrone.com/agriculture/, 3 pgs.

"Drones for Agriculture," SenseFly Ltd., retrieved on May 20, 2015, from https://www.sensefly.com/applications/agriculture.html, 5 pgs.

"eBee Ag—The Precision Agriculture Drone," retrieved on May 27, 2015, from https://www.sensefly.com/drones/ebee-ag.html, 7 pgs.

"The Drone for Precision Agriculture" Brochure, eBee senseFly, senseFly Ltd., 2014, 7 pgs.

Postflight Terra 3D Professional photogrammetry software, Feature List, Version 3.4, Release Date: Apr. 8, 2015, 2 pgs.

\* cited by examiner

AGRICULTURAL DRONE FOR USE IN LIVESTOCK MONITORING

TECHNICAL FIELD

The present invention relates generally to livestock in a feedlot or other area, and, more particularly, to a process and system for using an agricultural drone for monitoring the health and condition of livestock.

BACKGROUND OF THE INVENTION

Modern livestock operations employ a large percentage of beef cattle and other livestock fed by commercial feedlot operators. These businesses are often independent contractors which accept livestock (e.g., cattle) from farmers or ranchers at a certain size and age and feed them until they reach a designated size for slaughter. Typically, the farmer or rancher pays the commercial feedlot operator a rental fee for space and care in the feedlot pen(s) and for the associated feeding costs including other operating expenses.

In the feedlot, cattle are grouped in pens according to their feed requirements. Feedlots generally feed thousands of head of cattle or other livestock at various stages of growth. Cattle within a feedlot are physically contained in cattle pens where each pen will typically have a feed bunk to receive and hold feed for the cattle to consume. Ownership of particular cattle in the feedlot is defined by a unique lot number, for example, and the number of cattle in a particular feedlot can vary and may occupy a fraction of one or more cattle pens.

Within a particular pen, cattle are fed substantially the same feed ration (i.e., substantially the same ration type and quantity) and any one feedlot may have a large number of pens to accommodate cattle at various growth stages or that require special feed handling due to illness or malnourishment, for example. That is, livestock may be exposed to disease which can devastate a livestock population and be very costly to the owners. Each year large numbers of livestock are lost due to undetected or late detection of illness.

Considerable human labor is expended in monitoring the health and status of livestock in such feedlots (and other environments) including but not limited to monitoring certain physiological states. For example, a current practice for detection of sick livestock in typical feedlot operations is to employ a so-called "pen rider" who is an individual (e.g., a cowboy) responsible for riding about pens across the feedlot looking for individual livestock (e.g., cattle) that are exhibiting sickly characteristics. Such characteristics might include head down, reduced mobility, reduced alertness and runny noses. In addition to identifying such livestock, an important goal is to ultimately isolate the sick animals from the other livestock in the pen to reduce the risk of spreading any sickness and for treating the sick animals. Of course, as with any human centric activity, issues arise with respect to availability (i.e., finding enough capable workers to fill the need), effectiveness, consistency, speed, accuracy and a variety of working conditions that can make the job difficult for humans.

One critical physiological measure of determining livestock health is the core body temperature of the animal which can vary from a normal core body temperature due to a variety of conditions. For example, several hours before a cow is in standing heat and most likely to conceive, the core body temperature of the cow rises, or if the cow is sick or under heat stress from ambient conditions this may also cause a rise in temperature of the animal. Conversely, the temperature of the cow may drop shortly before delivery of a calf, or if the cow is experiencing hypothermia and/or if the cow has died.

As such, given that core body temperature is an important indicator of a variety of physiological states, there have been a number of techniques developed to measure temperature of livestock and/or reduce the human factor needed to collect such information. For example, U.S. Pat. Nos. 5,984,875, 6,059,733 and 6,099,482 describe an animal temperature system that utilizes ingestible boluses for monitoring physiological parameters of animals. Further, for example, U.S. Pat. No. 4,865,044 describes a temperature sensing system for cattle that utilizes a transmitter and encoding circuitry mounted on an ear tag which is connected to a temperature-sensing probe placed in the ear canal of the cattle being monitored, and U.S. Patent Application Publication No. 2002/0010390 describes a system for the automated monitoring of livestock and other animals that utilizes an implantable wireless "smart tele-sensor" that can be implanted in the animal which measures and transmits temperature and other parameters (e.g., blood oxygen and heart rate) related to the health and status of the animal being monitored. The transmitted temperature and other parameters are transmitted to human personnel carrying certain receiving devices (e.g., personal hand-operated radios, personal digital assistants or cell phones) to take corrective action and/or an off-site location for monitoring.

As will be appreciated, while a variety of animal temperature monitoring techniques exist the ability to rapidly deploy a complete, practical, efficient and cost effective temperature monitoring system for large-scale commercial livestock operations is beneficial.

Therefore, a need exists for an improved technique for reliably, efficiently and more effectively monitoring the temperature of livestock or other animals in large-scale commercial livestock operations.

BRIEF SUMMARY OF THE EMBODIMENTS

In accordance with various embodiments, one or more agricultural drones are used to improve the real-time monitoring, measuring and analysis of the health of livestock, in particular, the core body temperatures thereof.

More particularly, in accordance with an embodiment, one or more agricultural drones are dispatched to fly over one or more feedlots (or other large-scale livestock operations) having one or more pens associated therewith that hold a plurality of livestock. In accordance with the embodiment, the flying of the drone and the traversing of the feedlots allows the drone to monitor and examine one or more livestock in order to facilitate rapid and real-time measurement and analysis of at least the core body temperature of the individual livestock.

In accordance with an embodiment, the agricultural drone is configured with an imaging apparatus which includes a thermal imaging device and may also include further imaging devices such a general still camera, a video camera having a video recording function, a stereoscopic camera capable of obtaining a three-dimensional image using parallax, a 360 degree camera capable of obtaining 360 degree video, and/or a hyper-spectrum camera. For example, the thermal imaging device is a thermographic camera that forms an image using infrared radiation in a wavelength as long as 14,000 nm (i.e., in the infrared spectral band 7500-14,000 nm). Further, for example, a hyper-spectrum camera is used for obtaining an image having a wavelength band from near-ultraviolet (for example, 350 nm) to near-infrared (for example, 1100 nm) and splits the wavelength of the image at predetermined intervals (for example, 5 nm) using a diffraction grating or the like to obtain hyper spectrum information. This thermographic and/or hyper spectrum information facilitates the measurement of the core temperature of the animal(s) being monitored and an analysis to determine, for example, the current health condition of the animal. For example, the agricultural drone may communicate such temperature analysis information to a central location for processing by a livestock management control center to facilitate taking any corrective action necessary with respect to identified sick livestock. In accordance with an embodiment, the temperature analysis information may include measured temperature information, other images of the livestock (e.g., photographic images) taken by the agricultural drone that can be collectively utilized to assess the health of one or more livestock, and/or the location of the livestock.

In accordance with another embodiment, the agricultural drone may process such temperature analysis information directly while in-flight and communicate the need and/or appropriate action to be taken to a respective feed truck (or other agricultural truck) traversing the feedlot so that a human operator of the truck may take further corrective action and/or isolate the sick animal in a particular pen. In accordance with this embodiment, the flying of the agricultural drone and the traversing of the feed lots by the feed truck(s) occur substantially contemporaneously. As such, the agricultural drone communicates the collected temperature analysis information, as the drone flies over the feed lot, to the feed truck operating in some proximity to the drone so that the operator of the vehicle can utilize the information to take corrective action regarding an identified sick livestock during, illustratively, the delivery of feed to feed bunks associated with the pen. For example, to isolate the livestock within the pen or remove the livestock from pen. Similarly, in accordance with other embodiments, the agricultural drone may also communicate in real-time with one or more pen riders traversing the feed lot (e.g., on horseback) and/or a herd manager (e.g., monitoring the livestock from livestock management control center) to identify sick livestock and undertaking correction action.

These and other advantages of the embodiments will be apparent to those of ordinary skill in the art by reference to the following detailed description and the accompanying drawings.

DETAILED DESCRIPTION

In accordance with various embodiments, one or more agricultural drones are used to improve the real-time monitoring, measuring and analysis of the health of livestock, in particular, the core body temperatures thereof.

Figure 1:
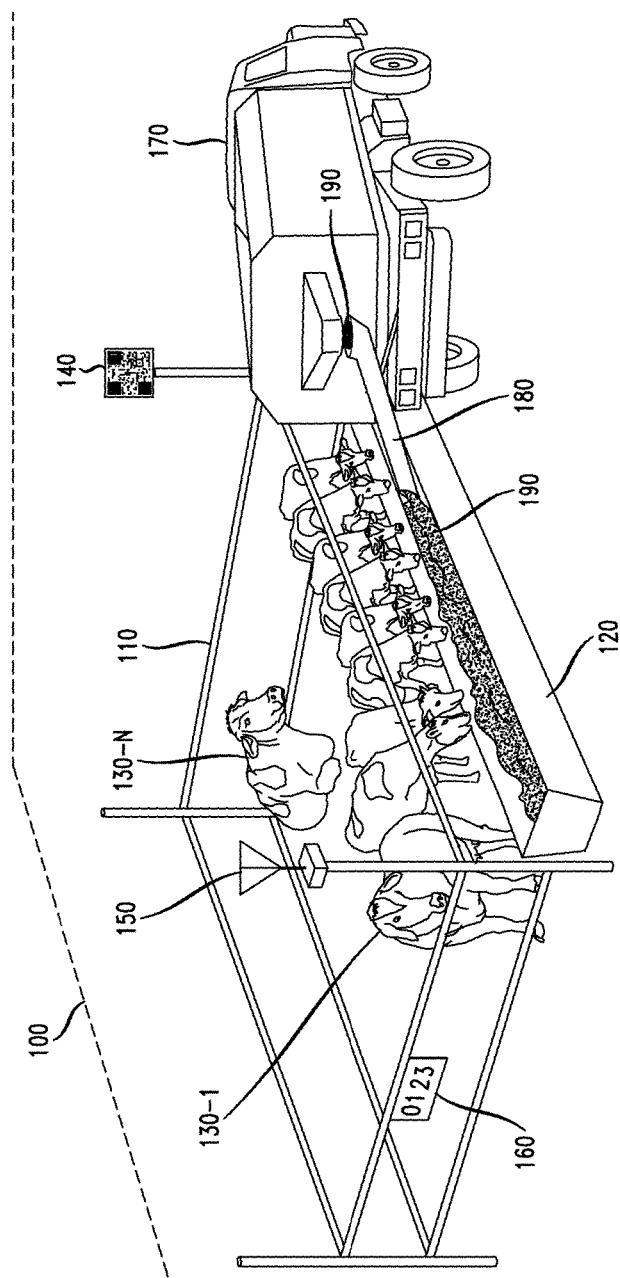
FIG. 1 shows an illustrative feedlot, feed bunk and feed truck arrangement for the caring and feeding of livestock in accordance with an embodiment.

FIG. 1 shows an illustrative feedlot 100, feed bunk 120 and feed truck 170 arrangement for the feeding of livestock. As shown, feedlot 100 has pen 110 holding a plurality of livestock (illustratively cattle 130-1 through cattle 130-N), feed bunk 120 for holding a ration (i.e., a type of feed, in a selected quantity) selected for the livestock contained by pen 110, i.e., cattle 130-1 through 130-N. Pen 110 has an associated identification symbol 160 to distinguish pen 110 from other pens (not shown) in feedlot 100 so that a driver of feed truck 170 driving by feedlot 100 can clearly distinguish pen 110 when reading feed bunk 120 or delivering feed 190 in a designated feed ration to feed bunk 120 by feed truck 170 through feed chute 180. Alternatively, the identification of pen 110 can be automated using an RF signal transmitted locally by transmitter 150 and/or by affixing bar code 140 to pen 110 for reading by a bar code scanner, and/or by using an associated GNSS location, for example. As will be appreciated, while a single pen, i.e., pen 110, is shown in feedlot 100 it will be understood that feedlot 100 can be a size of hundreds of miles with many feed bunks located throughout its geographic footprint. The driver of feed truck 170, in addition to feed delivery, may also be responsible for observing and monitoring the health of the livestock contained by pen 110, i.e., cattle 130-1 through 130-N.

Figure 2:
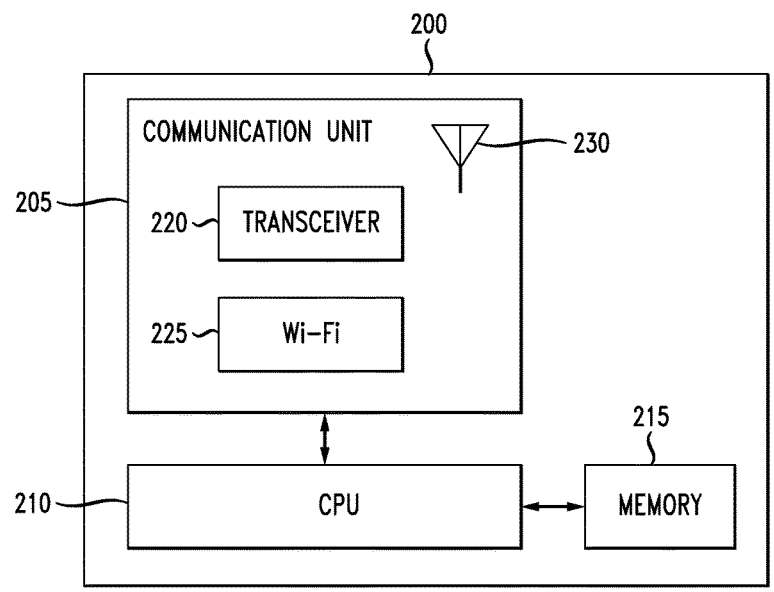
FIG. 2 shows a high-level block diagram of a livestock monitoring analysis unit which is integral with the feed truck of FIG. 1 in accordance with an embodiment.

In accordance with an embodiment, feed truck 170 is configured with livestock monitoring analysis unit 200 as shown in FIG. 2. Livestock monitoring analysis unit 200 includes communication unit 205 having transceiver 220, Wi-Fi controller 225 and antenna 230, central processing unit (CPU) 210, and memory 215. As detailed further herein below, livestock monitoring analysis unit 200, being integral with feed truck 170, will facilitate real-time communications between feed truck 170 and one or more agricultural drones flying in proximity thereto in order to improve the health monitoring of livestock in a feedlot. Further, in accordance with an embodiment, CPU 210 can execute certain livestock management application software (as stored in memory 215) for receiving and processing the temperature analysis information transmitted from the one or more agricultural drones, as detailed further herein below. Of course, as will be appreciated, while the embodiments described herein are with respect to pens, feedlots, and feed trucks it will be understood that the principles disclosed herein are not limited to such embodiments and are equally applicable to any large-scale livestock operation where the real-time monitoring, measuring and analysis of the health of livestock, in particular, their core body temperatures is desired.

Figure 3:
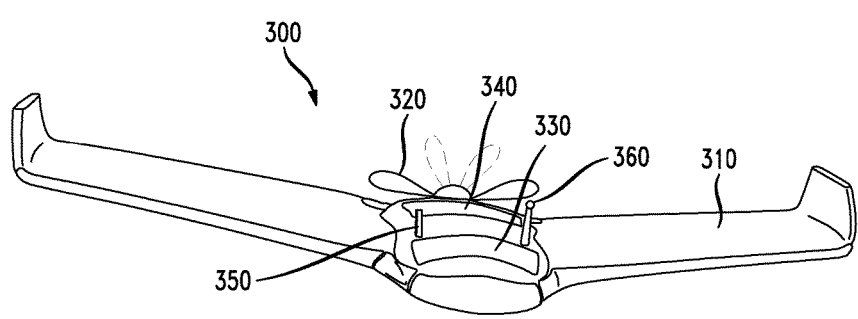
FIG. 3 shows an illustrative agricultural drone in accordance with an embodiment.

In particular, FIG. 3 shows an illustrative agricultural drone 300 in accordance with an embodiment. As shown, agricultural drone 300 includes a lightweight body and wings 310, motor assembly 320, built-in GNSS/RTK/PPP receiver 330, imaging apparatus 340, pitot tube 350 and antenna 360. Of course, agricultural drone 300 will include other components and functionality not depicted in FIG. 3 such as batteries, ground sensors, other onboard electronics and communications, onboard artificial intelligence, collision avoidance, to name a few. One such commercially available agricultural drone is the eBee Ag drone sold by senseFly Ltd, Route de Geneve 38, 033 Cheseaux-Lausanne, Switzerland. Agricultural drone 300 is fully autonomous and will fly in accordance with a predefined flight plan and in the case of agricultural applications the drone will capture highly accurate images of a particular field or fields and/or a particular feedlot or feedlots covering hundreds of hectares/acres in a single flight, and monitoring and measuring the health (e.g., core body temperature) of livestock in the field or fields in accordance with various embodiments.

In accordance with an embodiment, agricultural drone 300 is configured with imaging apparatus 340 which includes a thermal imaging device and may also include further imaging devices such a general still camera, a video camera having a video recording function, a stereoscopic camera capable of obtaining a three-dimensional image using parallax, a 360 degree camera capable of obtaining 360 degree video, and/or a hyper-spectrum camera. For example, the thermal imaging device is a thermographic camera that forms an image using infrared radiation in a wavelength as long as 14,000 nm (i.e., in the infrared spectral band 7500-14,000 nm). Further, for example, a hyper-spectrum camera is used for obtaining an image having a wavelength band from near-ultraviolet (for example, 350 nm) to near-infrared (for example, 1100 nm) and splits the wavelength of the image at predetermined intervals (for example, 5 nm) using a diffraction grating or the like to obtain hyper spectrum information.

Illustratively, imaging apparatus 340 as configured with the thermal imaging device (e.g., a laser or other such device) provides agricultural drone 300 with the ability to monitor the core body temperature of the livestock. This thermographic and/or hyper spectrum information facilitates the measurement of the core temperature of the animal(s) being monitored and analysis to determine, for example, the current health condition of the animal. For example, agricultural drone 300 may communicate such temperature analysis information to a central location for processing by a livestock management control center to facilitate taking any corrective action necessary with respect to an identified sick livestock (e.g., cattle 130-1 as shown in FIG. 1). For example, a herd manager resident at the livestock management control center may receive a warning signal from the agricultural drone 300 that a particular livestock is exhibiting a current temperature that is outside of a normal temperature range, and the herd manager may send a remote communication back to agricultural drone 300 that directs agricultural drone 300 to study that particular livestock (e.g., using imaging apparatus 340) more closely through still imaging, for example. In accordance with an embodiment, the temperature analysis information may include measured temperature information, other images of the livestock taken by the agricultural drone that can be collectively utilized to assess the health of one or more livestock, and/or the location of the particular "down" livestock that has been monitored. For example, a color photographic image of the livestock can be useful in conveying the current physical state of the livestock and possibly compared to prior stored images of that livestock to assist ascertaining the current physical state.

Figure 4:
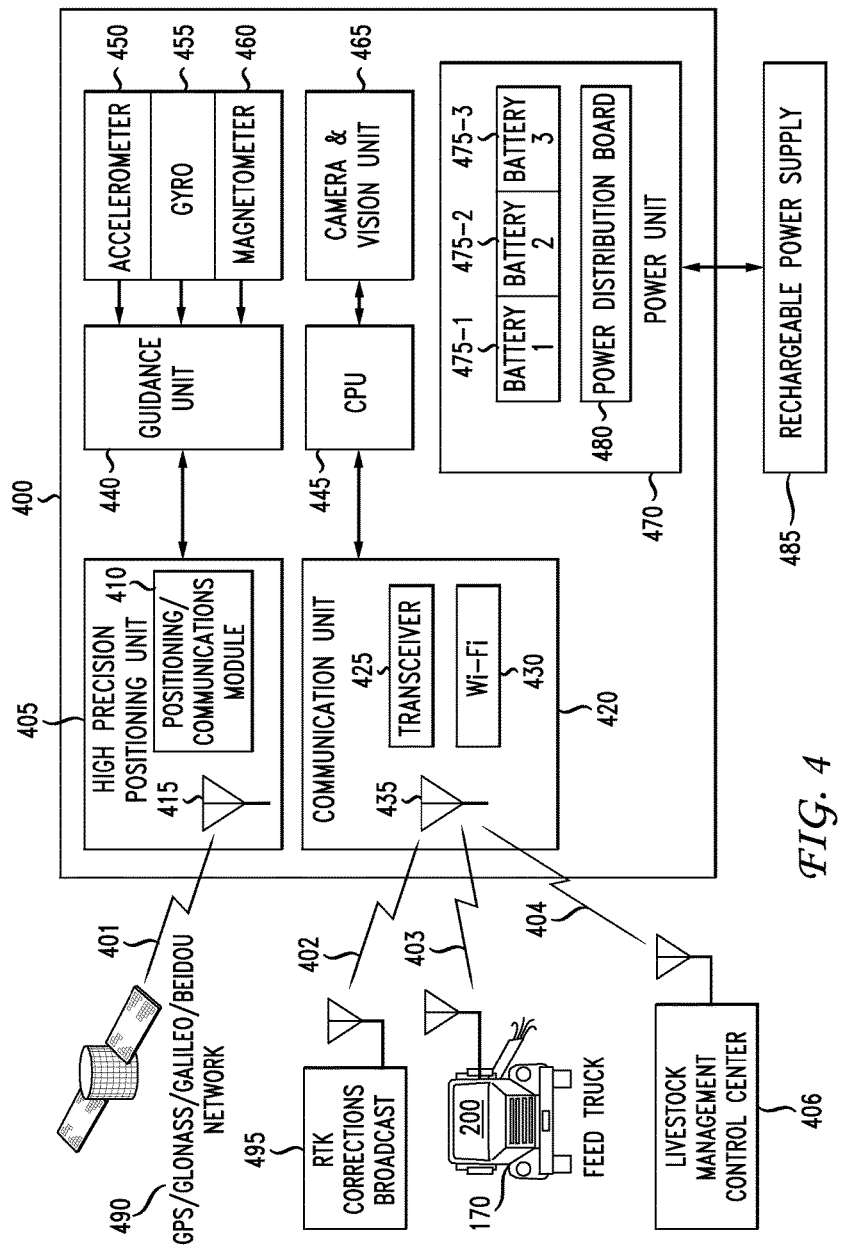
FIG. 4 shows a high-level block diagram of on-board electronics which is integral with the agricultural drone of FIG. 3 in accordance with an embodiment.

FIG. 4 shows a high-level block diagram of on-board electronics 400 which are integral with agricultural drone 300 of FIG. 3 in accordance with an embodiment. As shown, on-board electronics 400 includes high precision positioning unit 405 having positioning/communications module 410 (e.g., a GPS/GLONOSS/GALILEO/BEIDOU positioning/communications module) and antenna 415 which communicates, via communications link 401, with GPS/GLONOSS/GALILEO/BEIDOU network 490 in a well-known fashion, communication unit 420 having transceiver 425, Wi-Fi controller 430 and antenna 435 which interfaces with at least RTK corrections broadcast 495 over communications link 402 in a well-known fashion, guidance unit 440, central processing unit (CPU) 445, accelerometer 450, gyro 455, magnetometer 460, camera and vision unit 465 (forming imaging apparatus 340 shown in FIG. 3, in whole or in part), power unit 470 having batteries 475-1 through 475-3 and power distribution board 480 which interfaces with rechargeable power supply 485 in a well-known fashion. In accordance with various embodiments, agricultural drone 300 will transmit and communicate real-time communications and livestock health information regarding at least one physiological parameter (i.e., measured core body temperatures of particular ones of the livestock being monitored) to feed truck 170 as configured with livestock monitoring analysis unit 200 (as shown illustratively in FIG. 4), via communication link 403, utilizing communications unit 420 with respect to a particular feedlot under investigation by agricultural drone 300.

In accordance with further embodiments, agricultural drone 300 will transmit and communicate real-time communications and information to livestock management control center 406, via communication link 404, utilizing communications unit 420 with respect to a particular feedlot and/or livestock under investigation by agricultural drone 300, and a user (not shown) working in livestock management control center 406 may analyze the information received from agricultural drone 300 to determine if particular ones of the livestock are exhibiting any health issues and define what corrective action(s) to take. Of course, in a further embodiment, agricultural drone 300 may also transmit and communicate such real-time communications and information simultaneously to both feed truck 170 and livestock management control center 406. Similarly, in accordance with other embodiments, the agricultural drone may also communicate in real-time with one or more pen riders (not shown) traversing the feed lot and/or a herd manager (not shown) to identify sick livestock (e.g., monitoring the livestock from livestock management control center) and undertaking corrective action.

Figure 5:
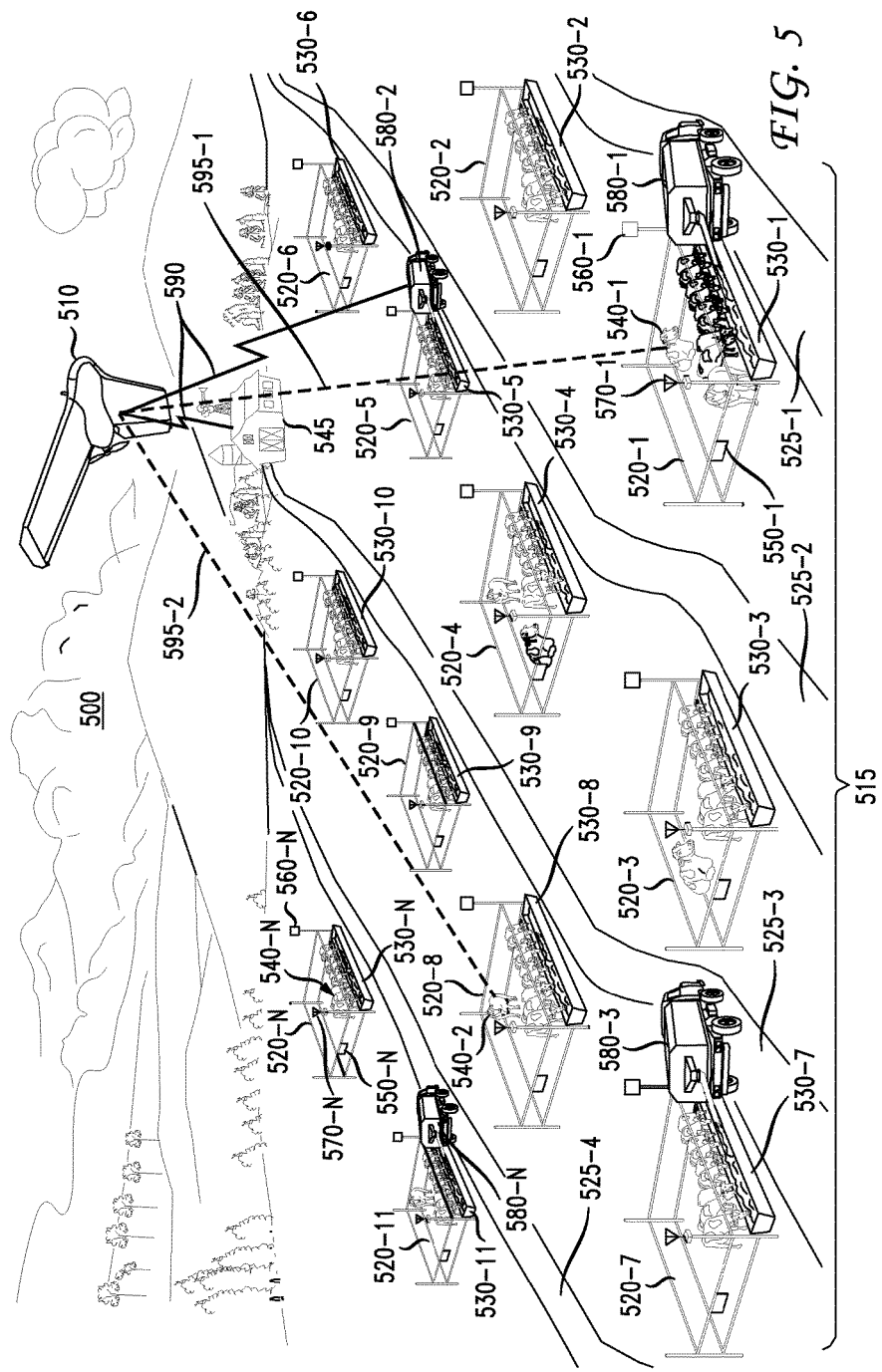
FIG. 5 shows an explanatory diagram of the use of the agricultural drone configured in accordance with FIG. 3 and FIG. 4 for monitoring the health of livestock in a feedlot in accordance with an embodiment.

FIG. 5 shows an explanatory diagram 500 of an embodiment the use of agricultural drone 510 configured in accordance with FIG. 3 and FIG. 4 for monitoring the health of livestock in a feedlot in accordance with an embodiment. Further, feed truck 580-1 through feed truck 580-N are each configured in accordance with FIG. 1 and FIG. 2 (as shown illustratively in FIG. 4) for interfacing, for example, with agricultural drone 510. As will be appreciated, while the description of the various embodiments herein utilize agricultural drones configured consistent with agricultural drone 300, the principles and advantages of the embodiments are not limited to such a drone and are equally useful and applicable to other types of drones and unmanned aerial vehicles having the same or similar configurations.

As shown, feed trucks 580-1 through 580-N are travelling along feed alley 525-1, feed alley 525-2, feed alley 525-3, and feed alley 525-4, as the case may be, that are routed through feedlot 515 for the delivery of feed rations to a plurality of feed bunks (i.e., feed bunk 530-1 through 530-N). As shown, agricultural drone 510 is flying over feedlot 515 having a plurality of pens (i.e., pen 520-1 through pen 520-N), with each respective pen holding one or more livestock (e.g., cattle 540-1 through 540-N) and configured with a particular one feed bunk of the plurality of feed bunks 530-1 through 530-N, a particular one transmitter (i.e., transmitter 570-1 through 570-N), a particular one bar code (i.e., bar code 560-1 through 560-N) and a particular one identification symbol (i.e., identification symbol 550-1 through 550-N). It will be understand that the plurality of livestock may be any kind (one or many) of livestock or other animals that are typically fed using feedlots or roaming in other large scale livestock populations.

The flyover by agricultural drone 510 will be in accordance with a defined flight plan in a well-known manner during which agricultural drone 510 will be collecting real-time information with respect to feedlot 515 and/or one or more of the livestock associated therewith (i.e., cattle 540-1 through cattle 540-N). In accordance with this embodiment, the flying of agricultural drone 510 and the traversing of feedlot 515 by feed trucks 580-1 through 580-N occur substantially contemporaneously. In accordance with further embodiments, agricultural drone 510 may fly in advance of the routing (in whole or in part) of feed trucks 580-1 through 580-N.

In accordance with the embodiment, the flying of agricultural drone 510 and the traversing of feedlot 515 (and associated pens 520-1 through 520-N) allows agricultural drone 510 to monitor and examine individual livestock (e.g., cattle 540-1) in order to facilitate rapid and real-time analysis and monitoring of the health of the livestock by measuring at least one physiological parameter, for example, at least their core body temperature (e.g., measuring the core body temperature of cattle 540-1). As such, in accordance with the embodiment, agricultural drone 510 is able to fly over the feedlot and plurality of livestock to scan for livestock that are "down" due to sickness or death, for example. Illustratively, such health monitoring and temperature measuring is accomplished as agricultural drone 510 flies over feedlot 515 and utilizes the image apparatus configured therein (i.e., imaging apparatus 340) to direct beam 595-1 at cattle 540-1 or direct beam 595-2 at cattle 540-2 which will measure the respective temperature of each by capturing a thermal image of cattle 540-1 and/or cattle 540-2 in a well-known fashion. Such thermal image is then used, in accordance with the embodiment, to determine the core body temperature of cattle 540-1 and/or cattle 540-2 to ascertain the animal's overall current health condition. In other words, in accordance with the embodiment, ascertaining the current physiological state of one or more of the plurality of cattle 540-1 through 540-N.

Illustratively, these thermal images can be examined using thermographic imaging software that will analyze the information transmitted and received from agricultural drone 510, either in real-time or at some future time. Further, illustratively, agricultural drone 510 may also capture other images (e.g., photographic images) of cattle 540-1 and/or cattle 540-2 from imaging apparatus 340 which can be useful in determining the current physiological state of cattle 540-1 and/or cattle 540-2. Further, as detailed above, agricultural drone 510 may be configured to also monitor and analyze the temperature(s) of the plurality of cattle 540-1 through 540-N itself to determine whether one or more of the animals are suffering from a current health issue and report the physiological state of the livestock as part of the information collected by the drone. In other words, in accordance with the embodiment, the agricultural drone 510 is able ascertain the current physiological state of one or more of the plurality of cattle 540-1 through 540-N.

Advantageously, in accordance with the embodiment, the real-time livestock health information collected by agricultural drone 510 such as thermal images and/or other images will be utilized and communicated, over one or more communications links 590, to livestock management control center 545 and/or one or more of the feed trucks 580-1 through 580-N to assist with monitoring the health of cattle 540-1 through 540-N. Communications links 590 are, illustratively, a wireless communications link established over wireless infrastructure, such as a third party supplied cellular or Wi-Fi network, but in many cases where an existing third party wireless infrastructure does not exist, the user must provide a suitable replacement. In such cases, one type of a user supplied infrastructure configuration is a narrowband single frequency radio system that may be operated over feedlot 515, for example. Such communication is realized with, for example, Wi-Fi radios as well as cellular phones (e.g., 3G/4G/LTE/5G), UHF radios and/or solid state radios.

As such, the real-time information collected, provided and transmitted by agricultural drone 510 allows for increased efficiency, speed and/or accuracy in the health monitoring of livestock which far exceeds that of traditional, labor intensive monitoring techniques. Further, given that the conditions associated with feedlot 515 can change rapidly due to a variety of adverse conditions (e.g., wind, rain, heat, etc.) that may also impact the health of the livestock (e.g., cattle 540-1 through 540-N), the application of agricultural drone 510 in real-time allows for a determination of their overall impact on the health of the livestock at any particular time.

Figure 6:
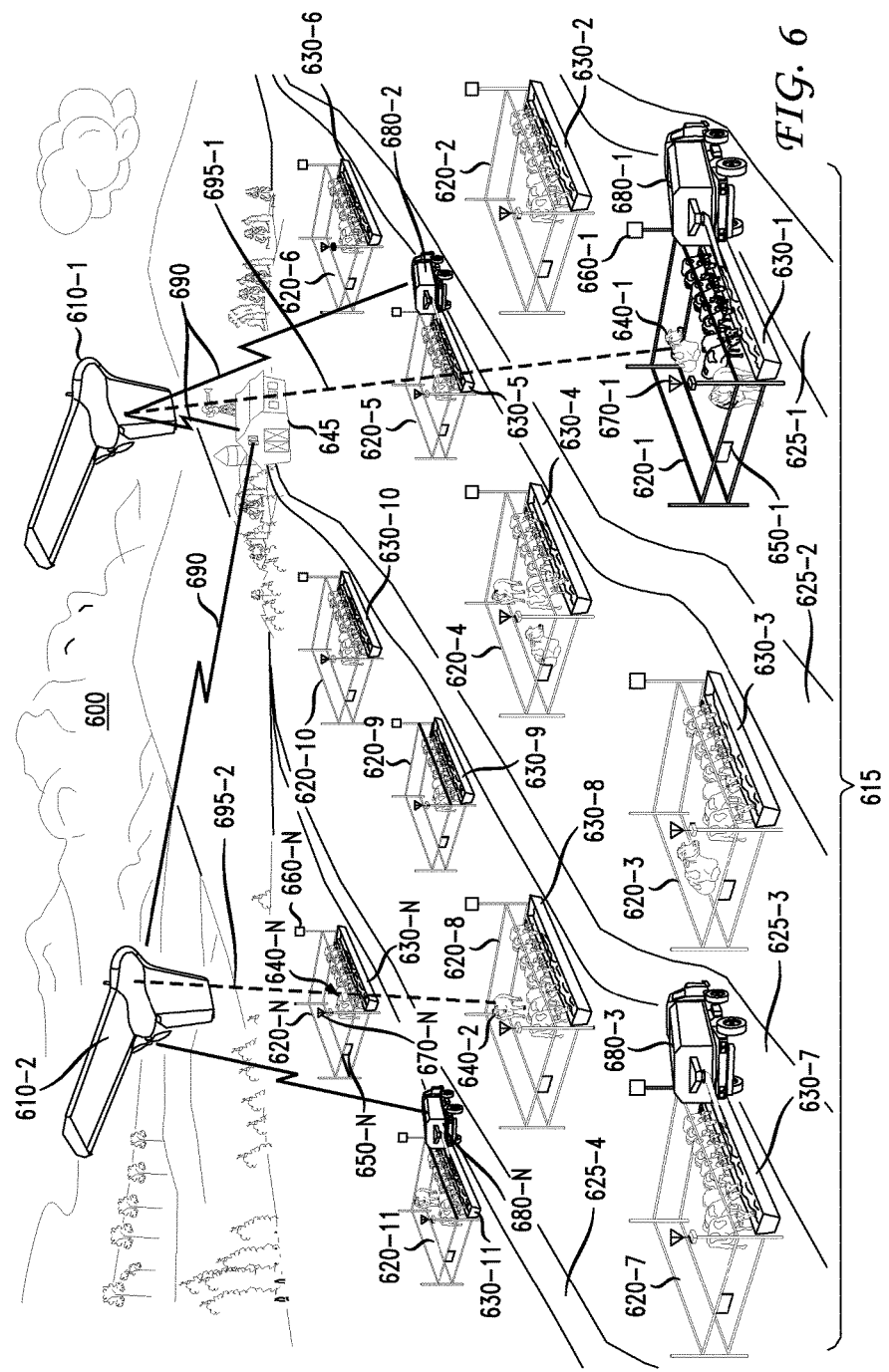
FIG. 6 shows an explanatory diagram of the use of multiple agricultural drones configured in accordance with FIG. 3 and FIG. 4 for monitoring the health of livestock in a feedlot in accordance with an embodiment.

FIG. 6 shows an explanatory diagram 600 of another embodiment use of multiple agricultural drones configured in accordance with FIG. 3 and FIG. 4 for monitoring the health of livestock in a feedlot in accordance with an embodiment. That is, agricultural drone 610-1 and agricultural drone 610-2 are each configured the same as agricultural drone 300 in accordance with FIG. 3 and FIG. 4 and flying over feedlot 615. Further, feed truck 680-1 through feed truck 680-N are each configured in accordance with FIG. 1 and FIG. 2 (as shown illustratively in FIG. 4). These flyovers by agricultural drone 610-1 and agricultural drone 610-2 will be in accordance with a defined flight plans in a well-known manner during which agricultural drone 610-1 and/or agricultural drone 610-2 will each be collecting real-time information with respect to feedlot 615 and/or the livestock associated therewith (i.e., cattle 640-1 through cattle 640-N). Of course, while FIG. 6 illustratively shows two drones it will be understood that any number of drones may be utilized in accordance with the principles of the embodiments.

As shown, feed trucks 680-1 through 680-N are travelling along feed alley 625-1, feed alley 625-2, feed alley 625-3, and feed alley 625-4, as the case may be, that are routed through feedlot 615 for the delivery of feed rations to a plurality of feed bunks (i.e., feed bunk 630-1 through 630-N). As shown, agricultural drone 610-1 and agricultural drone 610-2 are flying over feedlot 615 having a plurality of pens (i.e., pen 620-1 through pen 620-N), with each respective pen holding one or more livestock (e.g., cattle 640-1 through 640-N) and configured with a particular one feed bunk of the plurality of feed bunks 630-1 through 630-N, a particular one transmitter (i.e., transmitter 670-1 through 670-N), a particular one bar code (i.e., bar code 660-1 through 660-N) and a particular one identification symbol (i.e., identification symbol 650-1 through 650-N). It will be understand that the plurality of livestock may be any kind (one or many) of livestock or other animals that are typically fed using feedlots.

The flyover by agricultural drone 610-1 and agricultural drone 610-2 will be in accordance with a defined flight plan in a well-known manner during which these agricultural drones will be collecting real-time information with respect to feedlot 615 and/or one or more of the livestock associated therewith (i.e., cattle 640-1 through cattle 640-N). In accordance with this embodiment, the flying of agricultural drone 610-1 and agricultural drone 610-2 and the traversing of feedlot 615 by feed trucks 680-1 through 680-N occur substantially contemporaneously. In accordance with further embodiments, agricultural drone 610-1 and/or agricultural drone 610-2 may fly in advance of the routing (in whole or in part) of feed trucks 680-1 through 680-N. As such, in accordance with the embodiment, agricultural drone 610-1 and/or agricultural drone 610-2 are each able to fly over the feedlot and plurality of livestock to scan for livestock that are "down" due to sickness or death, for example.

In accordance with the embodiment, the real-time information collected by agricultural drone 610-1 and/or agricultural drone 610-2 such thermal images and/or other images will be utilized and communicated, over one or more communications links 690, to livestock management control center 645 and/or one or more of the feed trucks 680-1 through 680-N to assist with monitoring the health of one or more livestock (e.g., cattle 640-1 through 640-N). Further, communications can be exchanged by and between agricultural drone 610-1 and agricultural drone 610-2, in a well-known manner, in order to coordinate their actions and traversing of feedlot 615.

In accordance with the embodiment, the flying of agricultural drone 610-1 and agricultural drone 610-2 and the traversing of feedlot 615 (and associated pens 620-1 through 620-N and feed bunks 630-1 through 630-N) allows the drones, individually and collectively, to monitor and examine individual livestock in order to facilitate rapid and real-time analysis and monitoring of the health of the livestock by measuring at least one physiological parameter, for example, at least their core body temperature (e.g., measuring the core body temperature of cattle 640-1 and/or cattle 640-N). Illustratively, such health monitoring and temperature measuring is accomplished as agricultural drone 610-1 and/or agricultural drone 610-2 flies over feedlot 615 and utilizes the image apparatus configured therein (i.e., imaging apparatus 340) to direct beam 695-1 at cattle 640-1 and beam 695-2 at cattle 640-2, respectively, which will measure such temperature by capturing a thermal image of cattle 640-1 and cattle 640-2 in a well-known fashion. Such thermal image is then used, in accordance with the embodiment, to determine the core body temperature of cattle 640-1 and cattle 640-2 to ascertain each animal's overall current health condition.

Illustratively, these thermal images can be examined, in well-known fashion, using thermographic imaging software that will analyze the information transmitted and received from agricultural drone 610-1 and/or agricultural drone 610-2, either in real-time or at some future time. Further, illustratively, agricultural drone 610-1 and/or agricultural drone 610-2 may also capture other images (e.g., photographic images) of cattle 640-1 through 640-N from imaging apparatus 340 which can be useful in depicting the current physiological state of the animals. Further, as detailed above, agricultural drone 610-1 and/or agricultural drone 610-2 may be configured to also monitor and analyze the temperature(s) of the plurality of cattle 640-1 through 640-N themselves to determine whether one or more of the animals are suffering from a current health issue and report the physiological state of the livestock as part of the information collected by the drones. In other words, in accordance with the embodiment, the agricultural drones 610-1 and 610-2 are able to ascertain the current physiological state of one or more of the plurality of cattle 640-1 through 640-N.

Figure 7:
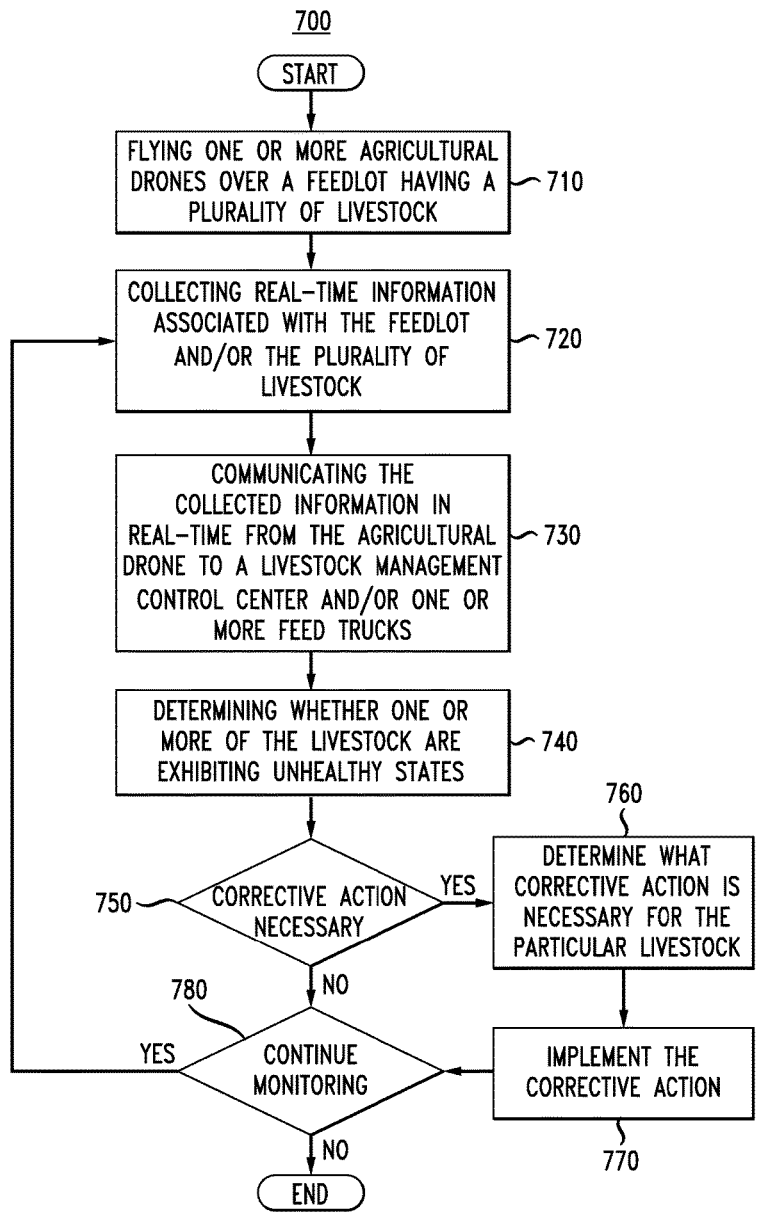
FIG. 7 shows a flowchart of illustrative operations for monitoring the health of livestock in a feedlot utilizing agricultural drone(s) in accordance with an embodiment.

FIG. 7 shows a flowchart of illustrative operations 700 for monitoring the health of livestock in a feedlot utilizing agricultural drone(s) in accordance with an embodiment. In accordance with the operations of FIG. 7, at step 710, one or more agricultural drones is flown over a feedlot having a plurality of livestock and, at step 720, collecting real-time information associated with the feedlot and/or the plurality of livestock (e.g., core body temperatures, as detailed herein above) from the agricultural drone. At step 730, the collected information is transmitted and communicated, in real-time, from the agricultural drone(s) to a livestock management control center and/or one or more feed trucks traversing the feedlot substantially contemporaneously with the agricultural drone(s), as detailed herein above, and, at step 740, a determination is made whether one or more of the livestock are exhibiting any unhealthy states and whether corrective action, step 750, is necessary. If corrective action is necessary, the corrective action is determined, at step 760, for the particular livestock and implemented at step 770, and monitoring of the livestock by the agricultural drone(s) continues as desired (step 780).

Advantageously, in accordance with the embodiment, the real-time livestock health information collected by agricultural drone (e.g., agricultural drone 610-1 or agricultural drone 610-2) such as thermal images and/or other images will be utilized and communicated, over one or more communications links (e.g., communication links 690), to a livestock management control center (e.g., livestock management control center 645) and/or one or more of the feed trucks (e.g., feed trucks 680-1 through 680-N) to assist with monitoring the health of the livestock (e.g., cattle 640-1 through 640-N), as detailed above.

Figure 8:
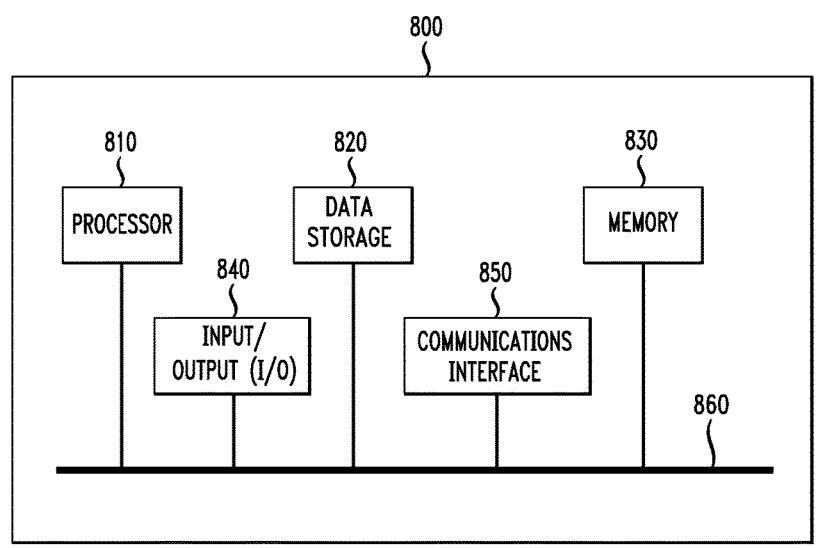
FIG. 8 is a high-level block diagram of a further exemplary livestock monitoring analysis unit in accordance with an embodiment.

As detailed above, the various embodiments herein can be embodied in the form of methods and apparatuses for practicing those methods. The disclosed methods may be performed by a combination of hardware, software, firmware, middleware, and computer-readable medium (collectively "communications device") installed in and/or communicatively connected to a processor or the like. FIG. 8 is a high-level block diagram of livestock monitoring analysis unit 800 which is an alternative configuration of exemplary livestock monitoring analysis unit 200 (as shown in FIG. 2) that may be used for monitoring the health of livestock in accordance with the various embodiments herein.

Livestock monitoring analysis unit 800 comprises a processor 810 operatively coupled to a data storage device 820 and a memory 830. Processor 810 controls the overall operation of livestock monitoring analysis unit 800 by executing computer program instructions that define such operations. Communications bus 860 facilitates the coupling and communication between the various components of livestock monitoring analysis unit 800. The computer program instructions may be stored in data storage device 820, or a non-transitory computer readable medium, and loaded into memory 830 when execution of the computer program instructions is desired.

Thus, certain of the steps of the disclosed method (see, e.g., FIG. 7) and the associated discussion herein above can be defined by the computer program instructions stored in memory 830 and/or data storage device 820 and controlled by processor 810 executing the computer program instructions. For example, the computer program instructions can be implemented as computer executable code programmed by one skilled in the art to perform the illustrative operations defined by the disclosed method. Accordingly, by executing the computer program instructions, processor 810 executes an algorithm defined by the disclosed method. Livestock monitoring analysis unit 800 also includes one or more communications interface 850 for communicating with other devices via a network (e.g., a wireless communications network) or communications protocol (e.g., Bluetooth®). For example, such communication interfaces may be a receiver, transceiver or modem for exchanging wired or wireless communications in any number of well-known fashions. Livestock monitoring analysis unit 800 also includes one or more input/output devices 840 that enable user interaction with livestock monitoring analysis unit 800 (e.g., camera, display, keyboard, mouse, speakers, microphone, buttons, etc.).

Processor 810 may include both general and special purpose microprocessors, and may be the sole processor or one of multiple processors of livestock monitoring analysis unit 800. Processor 810 may comprise one or more central processing units (CPUs), for example. Processor 810, data storage device 820, and/or memory 830 may include, be supplemented by, or incorporated in, one or more application-specific integrated circuits (ASICs) and/or one or more field programmable gate arrays (FPGAs).

Data storage device 820 and memory 830 each comprise a tangible non-transitory computer readable storage medium. Data storage device 820, and memory 830, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 840 may include peripherals, such as a camera, printer, scanner, display screen, etc. For example, input/output devices 840 may include a display device such as a cathode ray tube (CRT), plasma or liquid crystal display (LCD) monitor for displaying information to the user, a keyboard, and a pointing device such as a mouse or a trackball by which the user can provide input to livestock monitoring analysis unit 800.

It should be noted that for clarity of explanation, the illustrative embodiments described herein may be presented as comprising individual functional blocks or combinations of functional blocks. The functions these blocks represent may be provided through the use of either dedicated or shared hardware, including, but not limited to, hardware capable of executing software. Illustrative embodiments may comprise digital signal processor ("DSP") hardware and/or software performing the operation described herein. Thus, for example, it will be appreciated by those skilled in the art that the block diagrams herein represent conceptual views of illustrative functions, operations and/or circuitry of the principles described in the various embodiments herein. Similarly, it will be appreciated that any flowcharts, flow diagrams, state transition diagrams, pseudo code, program code and the like represent various processes which may be substantially represented in computer readable medium and so executed by a computer, machine or processor, whether or not such computer, machine or processor is explicitly shown. One skilled in the art will recognize that an implementation of an actual computer or computer system may have other structures and may contain other components as well, and that a high level representation of some of the components of such a computer is for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for monitoring a plurality of livestock, the method comprising:
    collecting real-time information specific to at least one livestock of the plurality of livestock from a first agricultural drone flying over the plurality of livestock, and wherein the real-time information specific to the at least one livestock collected includes image data of the at least one livestock;
    collecting real-time information with respect to a feedlot associated with the at least one livestock, and wherein the real-time information with respect to the feedlot collected includes a plurality of adverse conditions, and wherein at least one of the adverse conditions of the plurality of adverse conditions is impacting the health of the at least one livestock, the at least one of the adverse conditions being a wind condition, a rain condition, or a heat condition;
    analyzing, by the first agricultural drone and based on the real-time information specific to the at least one livestock collected and the real-time information with respect to the feedlot collected, at least one physiological parameter to ascertain the physiological state of the at least one livestock, the at least one physiological parameter being a current core temperature associated with the at least one livestock;
    determining, by the first agricultural drone, whether the current core temperature is outside a normal temperature range associated with the at least one livestock, and if so, generating a first warning signal that the at least one livestock is exhibiting the current core temperature that is outside the normal temperature range; and
    transmitting the real-time information specific to the at least one livestock collected and the real-time information with respect to the feedlot collected and the first warning signal specific to the at least one livestock in real-time from the first agricultural drone for monitoring the at least one physiological state of the at least one livestock of the plurality of livestock.

2. The method of claim 1 further comprising:
    measuring, by the first agricultural drone, at least one other physiological parameter of the at least one least livestock, the at least one other physiological parameter included in the collected information; and transmitting the at least one other physiological parameter measured as part of the collected information.

3. The method of claim 1 further comprising:

receiving the real-time information specific to the at least one livestock collected and the real-time information with respect to the feedlot collected and the first warning signal at a livestock management control center; and sending, from the livestock management control center, a remote communication to the first agricultural drone, the remote communication directing the first agricultural drone to further analyze the at least one livestock.

4. The method of claim 1 further comprising: collecting real-time information specific to at least one other livestock of the plurality of livestock from a second agricultural drone, and wherein the real-time information specific to the at least one other livestock collected includes image data of the at least one other livestock, and the second agricultural drone flying contemporaneously with the first agricultural drone;

collecting real-time information with respect to a feedlot associated with the at least one other livestock, and wherein the real-time information with respect to the feedlot collected includes a plurality of adverse conditions, and wherein at least one of the adverse conditions of the plurality of adverse conditions is impacting the health of the at least one other livestock, the at least one of the adverse conditions being a wind condition, a rain condition, or a heat condition;

analyzing, by the second agricultural drone and based on the real-time information specific to the at least one other livestock collected and the real-time information with respect to the feedlot collected by second agricultural drone, at least one physiological parameter to ascertain the physiological state of the at least one other livestock, the at least one physiological parameter being a current core temperature associated with the at least one other livestock;

determining, by the second agricultural drone, whether the current core temperature is outside a normal temperature range associated with the at least one other livestock, and if so, generating a second warning signal that the at least one other livestock is exhibiting the current core temperature that is outside the normal temperature range; and transmitting the real-time information specific to the at least one other livestock collected and the real-time information with respect to the feedlot collected and the second warning signal specific to the at least one other livestock in real-time from the second agricultural drone for monitoring at least one physiological state of the at least one other livestock.

5. The method of claim 4 further comprising:

measuring, by the second agricultural drone, at least one physiological parameter of the at one other least one other livestock, the at least one physiological parameter included in the collected information; and transmitting the at least one physiological parameter measured as part of the collected information specific to the at least one other livestock.

6. The method of claim 5 wherein the real-time information specific to the at least one other livestock collected is transmitted in real-time from the second agricultural drone to at least one feed truck traversing a feedlot associated with the plurality of livestock.

7. The method of claim 1 wherein the image data includes a thermal image of the at least one livestock.

8. The method of claim 7 wherein the collected information includes a location of the at least one livestock.

9. The method of claim 3 wherein the transmitting the information specific to the at least one livestock collected and the real-time information with respect to the feedlot collected and the first warning signal specific to the at least one livestock is to the livestock management control center.

10. The method of claim 2 further comprising:

isolating the at least one livestock based on the real-time information specific to the at least one livestock collected.

11. The method of claim 3 wherein the plurality of livestock are associated with a feedlot.

12. The method of claim 7 wherein the image data includes a photographic image of the at least one livestock.

13. The method of claim 6 wherein the at least one feed truck is traversing the feedlot contemporaneously with the flying of the first agricultural drone and the second agricultural drone.

14. The method of claim 3 further comprising:

receiving, by the first agricultural drone, the remote communication;

transmitting, by the first agricultural drone, a real-time color photographic image of the at least one livestock conveying a current physical state of the at least one livestock; and determining, using the real-time color photographic image, whether a corrective action is necessary with respect to the at least one livestock.

15. A system for monitoring a plurality of livestock, the system comprising:

a first agricultural drone configured to fly over the plurality of livestock, and to (i) collect real-time information specific to at least one livestock of the plurality of livestock and wherein the real-time information specific to the at least one livestock collected includes image data of the at least one livestock, and real-time information with respect to a feedlot associated with the at least one livestock and wherein the real-time information with respect to the feedlot collected includes a plurality of adverse conditions, and wherein at least one of the adverse conditions of the plurality of adverse conditions is impacting the health of the at least one livestock, the at least one of the adverse conditions being a wind condition, a rain condition, or a heat condition, (ii) analyze, from the collected real-time information specific to the at least one livestock and the real-time information with respect to the feedlot at least one physiological parameter to ascertain the physiological state of the at least one livestock, the at least one physiological parameter being a current core temperature associated with the at least one livestock, (iii) determine whether the current core temperature is outside a normal temperature range associated with the at least one livestock, and if so, generate a first warning signal that the at least one livestock is exhibiting the current core temperature that is outside the normal temperature range, and (iv) transmit the collected real-time information specific to the at least one livestock and the real-time information with respect to the feedlot and the first warning signal specific to the at least one livestock in real-time from the first agricultural drone for monitoring at least one physiological state of the at least one livestock.

16. The system of claim 15 wherein a livestock management control center is configured to (i) receive the collected information, the real-time information with respect to a feedlot associated with the at least one livestock and the first warning signal specific to the at least one livestock from the first agricultural done in real-time, (ii) transmit a remote communication to the first agricultural drone, the remote communication directing the first agricultural drone to further study the at least one livestock, (iii) receive a color photographic image from the first agricultural drone in response to the remote communication, (iv) and determine if any corrective action is necessary based on the collected information and the color photographic image specific to the at least one livestock from the first agricultural drone.

17. The system of claim 15 wherein the first agricultural drone is further configured to measure at least one physiological parameter of the at least one least livestock, and transmit the at least one physiological parameter measured as part of the collected information.

18. The system of claim 16 wherein the livestock management control center is further configured to compare the current color photographic image of the at least one livestock to one or more previously stored color images of the at least one livestock.

19. The system of claim 18 wherein the corrective action is determined based on the comparison of the current color photographic image to the one or more previously stored color images.

20. The system of claim 15 further comprising:
a second agricultural drone configured to fly over the plurality of livestock, and to (i) collect real-time information specific to at least one other livestock of the plurality of livestock and wherein the real-time information specific to the at least one livestock collected includes image data of the at least one livestock, and real-time information with respect to a feedlot associated with the at least one other livestock, wherein the real-time information with respect to the feedlot collected includes a plurality of adverse conditions, and wherein at least one of the adverse conditions of the plurality of adverse conditions is impacting the health of the at least one other livestock, the at least one of the adverse conditions being a wind condition, a rain condition, or a heat condition, (ii) analyze, from the collected real-time information specific to the at least one other livestock and the real-time information with respect to the feedlot at least one physiological parameter to ascertain the physiological state of the at least one other livestock, the at least one physiological parameter being a current core temperature associated with the at least one other livestock, (iii) determine whether the current core temperature is outside a normal temperature range associated with the at least one other livestock, and if so, generate a second warning signal that the at least one other livestock is exhibiting the current core temperature that is outside the normal temperature range, and (iv) transmit the collected real-time information and the second warning signal specific to the at least one other livestock in real-time from the second agricultural drone for monitoring a physiological state of the at least one other livestock.

21. The system of claim 20 wherein the first agricultural drone and the second agricultural drone are configured to fly contemporaneously.

22. The system of claim 21 wherein at least one feed truck of a plurality of feed trucks receives the collected information specific to the at least one other livestock from the second agricultural drone in real-time.

23. The system of claim 20 wherein the first agricultural drone and the second agricultural drone are configured to communicate with each other.

24. The system of claim 17 wherein the first agricultural drone is further configured to capture a thermal image of the at least one livestock and determine the current core temperature therefrom.

25. The system of claim 20 wherein the second agricultural drone is further configured to capture a thermal image of the at least one livestock and determine the current core temperature therefrom.

26. A method for operating an agricultural drone, the method comprising:
flying the agricultural drone over a plurality of livestock;
collecting real-time information specific to the plurality of livestock from the agricultural drone, and wherein the real-time information specific to at least one livestock collected includes image data of the at least one livestock;
collecting real-time information with respect to a feedlot associated with the plurality of livestock, wherein the real-time information with respect to the feedlot collected includes a plurality of adverse conditions, and wherein at least one of the adverse conditions of the plurality of adverse conditions is impacting the health of the at least one livestock, the at least one of the adverse conditions being a wind condition, a rain condition, or a heat condition;
analyzing, by the agricultural drone using the real-time information specific to the at least one livestock collected and the real-time information with respect to the feedlot collected, at least one physiological parameter to ascertain the physiological state of at least one livestock of the plurality of livestock, the at least one physiological parameter being a current core temperature associated with the at least one livestock;
determining, by the agricultural drone, whether the current core temperature is outside a normal temperature range associated with the at least one livestock, and if so, generating a warning signal that the at least one livestock is exhibiting the current core temperature that is outside the normal temperature range; and
transmitting, by the agricultural drone, the real-time information specific to the at least one livestock collected and the real-time information with respect to the feedlot collected and the warning signal specific to the plurality of livestock in real-time from the agricultural drone for monitoring the health of the at least one livestock and particular other ones of the livestock of the plurality of livestock.

27. The method of claim 26 further comprising:
measuring, by the agricultural drone, at least one physiological parameter of the particular ones of the livestock, the at least one physiological parameter included in the collected information; and
transmitting the at least one physiological parameter measured for the particular ones of the livestock as part of the collected information.

28. The method of claim 27, further comprising:
receiving a remote communication, the remote communication directing the agricultural drone to further study the at least one livestock; and
transmitting, in response to the remote communication received, a current color photographic image of the at least one livestock.

29. The method of claim 28 further comprising:
   isolating one or more of the particular ones of livestock based on the collected information.

30. The method of claim 29 wherein the image data includes thermal images of the particular ones of the livestock.

31. The method of claim 30 wherein the image data includes photographic images of the particular ones of the livestock.

32. The method of claim 28 further comprising:
   determining a corrective action specific to the at least one livestock based on a comparison of the current color photographic image of the at least one livestock to one or more previously stored color images of the at least one livestock.

* * * * *